US008251887B2

(12) United States Patent
Li et al.

(10) Patent No.: US 8,251,887 B2
(45) Date of Patent: Aug. 28, 2012

(54) REPRODUCTIVE TECHNOLOGY OF LOW DOSE SEMEN PRODUCTION AND IN VITRO/IN VITRO FERTILIZATION IN DOMESTIC ANIMALS

(76) Inventors: Xihe Li, Huhhot (CN); Wenzhong Zhou, Beijing (CN); Guofu Zhang, Huhhot (CN); Songjin Qian, Tongliao (CN); Jiangguo Wang, Huhhot (CN)

( * ) Notice: Subject to any disclaimer, the term of this patent is extended or adjusted under 35 U.S.C. 154(b) by 742 days.

(21) Appl. No.: 12/321,704

(22) Filed: Jan. 24, 2009

(65) Prior Publication Data

US 2010/0191041 A1 Jul. 29, 2010

(51) Int. Cl.
*A61D 7/00* (2006.01)
*A01N 1/00* (2006.01)
*A01N 1/02* (2006.01)

(52) U.S. Cl. .............................. 600/35; 435/1.1; 435/2
(58) Field of Classification Search .................... 600/35; 435/1.1, 2

See application file for complete search history.

(56) References Cited

U.S. PATENT DOCUMENTS

| | | | | |
|---|---|---|---|---|
| 4,094,972 | A * | 6/1978 | Marquez | 424/561 |
| 4,267,268 | A | 5/1981 | Nelson, Jr. | |
| 4,362,246 | A | 12/1982 | Adair | |
| 5,135,759 | A | 8/1992 | Johnson | |
| 5,691,133 | A * | 11/1997 | Critser et al. | 435/2 |
| 5,770,363 | A | 6/1998 | Brown | |
| 5,972,592 | A | 10/1999 | Suarez | |
| 6,071,689 | A | 6/2000 | Seidel et al. | |
| 6,149,867 | A | 11/2000 | Seidel et al. | |
| 6,372,422 | B1 | 4/2002 | Seidel et al. | |
| 6,524,860 | B1 * | 2/2003 | Seidel et al. | 436/63 |
| 7,070,917 | B1 * | 7/2006 | Christensen et al. | 435/2 |
| 7,094,527 | B2 | 8/2006 | Seidel et al. | |
| 7,169,548 | B2 | 1/2007 | Maxwell et al. | |
| 7,195,920 | B2 | 3/2007 | Seidel et al. | |
| 7,208,265 | B1 | 4/2007 | Schenk | |
| 7,221,453 | B2 | 5/2007 | Sharpe et al. | |
| 7,371,517 | B2 | 5/2008 | Evans et al. | |
| 7,485,769 | B2 * | 2/2009 | Murakami et al. | 800/17 |
| 7,501,554 | B2 * | 3/2009 | Chen et al. | 800/14 |
| 7,674,576 | B2 * | 3/2010 | Loskutoff et al. | 435/2 |
| 7,741,311 | B2 * | 6/2010 | Mousa et al. | 514/54 |
| 7,781,207 | B2 * | 8/2010 | Lindenberg | 435/303.1 |
| 7,833,147 | B2 * | 11/2010 | Graham | 600/35 |
| 7,968,762 | B2 * | 6/2011 | Vande Woude et al. | 800/18 |
| 7,989,675 | B2 * | 8/2011 | Welsh et al. | 800/3 |
| 2004/0031071 | A1 * | 2/2004 | Morris et al. | 800/21 |
| 2005/0053910 | A1 | 3/2005 | McKenzie et al. | |
| 2006/0121440 | A1 | 6/2006 | Schenk et al. | |
| 2011/0082329 | A1 * | 4/2011 | Szabo | 600/35 |
| 2011/0086336 | A1 * | 4/2011 | Herickhoff et al. | 435/2 |
| 2011/0105835 | A1 * | 5/2011 | Magistrini et al. | 600/35 |
| 2011/0183934 | A1 * | 7/2011 | Ellington et al. | 514/54 |

FOREIGN PATENT DOCUMENTS

| | | |
|---|---|---|
| CN | 1732983 A | 2/2006 |
| CN | 1927226 A | 3/2007 |
| CN | 101220345 A | 7/2008 |
| JP | 2008-63235 | 3/2008 |

OTHER PUBLICATIONS

Baccetti et al., Infertile spermatozoa in a human carrier of robertsonian translocation 14;22. Fertility and Sterility 78(5) : 1127 (2002).*
Perez-Carnelo et al., Post-thaw viability of European bison (Bison bonasus) semen frozen with extenders containing egg yolk or lipids of plant origin and examined with a heterologous in vitro fertilization assay. Journal of Zoo and Wildlife Medicine 37(2) : 116 (2006).*
Garner et al.,Seminal plasma addition attenuates the dilution effect in bovine sperm. Theriogenology 56 : 31 (2001).*
Kaeoket et al., A preliminary study on using autologous and heterologous boar sperm supernatant from freezing processes as post-thawing solution: its effect on sperm motility. Tropical Animal Health and Production 43 : 1049 (2011).*
Parks et al., Cryopreservation of peregrine falcon semen and post-thaw dialysis to remove glycerol. Raptor Research20(1) :15 (1986).*
Roth et al., Scimitar-horned oryx (Oryx dammah) spermatozoa are functionally competent in a heterologous bovine in vitro fertilization system after cryopreservation on dry ice, in a dry shipper, or over liquid nitrogen vapor. Biology of Reproduction 60:493 (1999).*
Suquet et al. Cryopreservation of sperm in marine fish. Aquaculture Research 31(3) : 231 (2000).*
Tiersch T., Strategies for commercialization of cryopreserved fish semen. Revista Brasileira de Zootecnia 37 :15 (2008).*
Vogt et al., Human Y chromosome azoospermia factors (AZF) mapped to different subregions in Yq11. Human Molecular Genetics 5(7) : 933 (1996).*
Wang et al., "Study on Application of Frozen Sexed X-Semen of Dairy Cow AI", Journal of Guangxi Agric. and Biol. Science, vol. 25, Sep. 2006, p. 192.
Liu et al., "Research Progress of Factors Affecting the Quality of Silage", China Cattle Science, vol. 32 No. 5, Sep. 2006, pp. 59-66.
Moussa et al., "Low density lipoproteins extracted from hen egg yolk by an easy method: cryoprotective effect on frozen-thawed bull semen", Theriogenology 57, 2002, pp. 1695-1706. Tartaglione et al., "Prognostic value of spermatological parameters as predictors of in vitro fertility of frozen-thawed bull semen", Theriogenology 62, 2004, pp. 1245-1252.
http://www.beefsemenonline.co.uk/misc/hiahfertility.htm, High Fertility Semen, World Class Genetics Beef Semen Online, Mixed Semen, printed out Mar. 11, 2009 one page.
Ryder, Neil, Genus mixed-semen service increases conception rates, Farmers Guardian, Jan. 17, 2003, p. 70 (two total printed pages).
Beatty, R.A., Fertility of Mixed Semen From Different Rabbits, Journal of Reprod. Fertil., 1960, vol. 1, pp. 52-60.
Azmal, S.A., et al., Relative Merits of Homo and Heterospermic Bull Semen in Respect of Preservation Quality, Pakistan Journal of Biological sciences 7 (11), 2004, pp. 1908-1911.
U.S. Appl. No. 10/081,955, filed Feb. 20, 2002.
U.S. Appl. No. 10/556,981, filed Nov. 15, 2005.
U.S. Appl. No. 10/398,796, filed Apr. 3, 2003.
U.S. Appl. No. 10/879,480, filed Jun. 21, 2001.
U.S. Appl. No. 10/523,268, filed Jan. 31, 2005.
U.S. Appl. No. 10/522,320, filed Jan. 24, 2005.
U.S. Appl. No. 10/524,793, filed Feb. 15, 2005.

(Continued)

*Primary Examiner* — Ethan C Whisenant (74) *Attorney, Agent, or Firm* — Cindee R. Ewell; Ryan S. Christensen (57) ABSTRACT

Artificial insemination of female animals and in vitro fertilization of oocytes with fresh or frozen-thawed semen have been applied to the reproduction of animals. According to the traditional theory and conventional procedures, a great number of sperm cells are needed to ensure a successful fertilization.

15 Claims, 3 Drawing Sheets

OTHER PUBLICATIONS

U.S. Appl. No. 11/219,607, filed Sep. 2, 2005.
U.S. Appl. No. 11/004,382, filed Dec. 3, 2004.
U.S. Appl. No. 11/536,576, filed Sep. 28, 2006.
PCT Patent Application No. PCT/US2006/013082, filed Apr. 6, 2006.
U.S. Appl. No. 11/608,079, filed Dec. 7, 2006.
U.S. Appl. No. 11/608,039, filed Dec. 7, 2006.
U.S. Appl. No. 11/508,133, filed Aug. 21, 2006.
U.S. Appl. No. 11/536,492, filed Sep. 28, 2006.
U.S. Appl. No. 11/613,605, filed Dec. 20, 2006.
PCT Patent Application No. PCT/US2006/028846, filed Jul. 24, 2006.
U.S. Appl. No. 11/442,735, filed May 25, 2006.
U.S. Appl. No. 11/668,148, filed Jan. 29, 2007.
U.S. Appl. No. 11/400,839, filed Apr. 6, 2006.
U.S. Appl. No. 11/804,879, filed May 21, 2007.
PCT Patent Application No. PCT/US2007/014724, filed Jun. 26, 2007.
U.S. Appl. No. 11/805,572, filed May 22, 2007.
U.S. Appl. No. 10/812,351, filed Mar. 29, 2004.
U.S. Appl. No. 10/811,593, filed Mar. 29, 2004.
U.S. Appl. No. 11/092,509, filed Mar. 29, 2005.
U.S. Appl. No. 11/092,313, filed Mar. 29, 2005.
U.S. Appl. No. 11/572,376, filed Jul. 22, 2005.
U.S. Appl. No. 11/092,338, filed Mar. 29, 2005.
U.S. Appl. No. 12/113,684, filed May 1, 2008.
U.S. Appl. No. 10/266,562, filed Oct. 7, 2002.
PCT Patent Application No. PCT/US2005/043926, filed Dec. 2, 2005.
Yassen, A.M. et al., Freezability of Bovine Spermatozoa in Tris-Buffered Yolk Extenders Containing Different Levels of Tris, Sodium, Potassium and Calcium Ions, J. Dairy Science vol. 50, No. 6, 1967, pp. 887-892.
Azmal, et al.; "Relative Merits of Homo and Heterospermic Bull Semen in Respect of Preservation Quality"; Article, Nov. 2004, pp. 1908-1911; vol. 7 (11), Pakistan Journal of Biol. Science (4 pages).
Beatty, R. A.; "Fertility of Mixed Semen From Different Rabbits"; Article, Feb. 1960, pp. 52-60, vol. 1, Journal of Reprod. Fertil. (9 pages).
Foote, R.H., "Buffers and Extenders: What Do They Do? Why Are They Important?"; Article, 1984, pp. 62-70; Proc of the NAAB Tech. Conf. on Artificial Insemination and Reproduction, USA (9 pages).
US Office Action dated Jun. 20, 2012 issued in corresponding U.S. Appl. No. 12/587,909 (12 pages).
Foote, R. H.,; "The History of artificial Insemination: Selected Notes and Notables"; Article, 2002, pp. 1-10, Published by the American Society of Animal Science USA (13 pages).
Definition of "Heterogeneous" found in the Merriam-Webster Dictionary (Online on Jun. 14, 2012) (1 page).
Napier, R.A.N.; "Fertility in the Male Rabbit: III. Estimation of Spermatozoan quality by Mixed Insemination, and the Inheritance of Spermatozoan Characters"; Article, 1961, pp. 273-289, vol. 2, Journal Reproduction and Fertility USA (17 pages).

* cited by examiner

REPRODUCTIVE TECHNOLOGY OF LOW DOSE SEMEN PRODUCTION AND IN VITRO/IN VITRO FERTILIZATION IN DOMESTIC ANIMALS

BACKGROUND

Artificial insemination of female animals and in vitro fertilization of oocytes with fresh or frozen-thawed semen have been applied to the reproduction of animals. According to the traditional theory and conventional procedures, a great number of sperm cells are needed to ensure a successful fertilization.

However, semen from certain animals and sex-selected inseminates which are produced by separating X-chromosome bearing sperm cells from Y-chromosome bearing sperm cells can be in limited supply. Additionally, the sperm cells of certain animals and sex-selected inseminates can have reduced fertility or cannot achieve the threshold of fertility in the context of conventional procedures for successful fertilization. In the cases of limited specific genetic resources, or the spermatozoa of the semen can not reach the threshold of fertility, a complementary technology is needed to solve the problems.

The inventive reduced dose inseminate (or low dose inseminate) described-herein addresses each of the above-described problems.

SUMMARY OF THE INVENTION

Accordingly, a broad object of the invention can be to provide a method for producing and using a reduced dose inseminate to fertilize the eggs of a female animal by artificial insemination with fewer sperm cells than compared with conventional dose inseminates.

Another broad object of the invention can be to provide a reduced dose inseminate which includes fewer sperm cells to achieve fertilization by conventional artificial insemination which increases the usage of rare genetic resources and lowers the cost of embryo production.

Another broad object of the invention can be provide a reduced dose inseminate to treat infertility due to low numbers of sperm cells or low numbers of fertile sperm cells, or poor activity of sperm cells.

Naturally, further objects of the invention are disclosed throughout other areas of the specification, drawings, photographs, and claims.

DETAILED DESCRIPTION OF THE PREFERRED EMBODIMENTS

Generally, a reduced dose inseminate produced by combining an amount of paternal semen of a paternal animal with an amount of heterogeneous semen of a heterogeneous male animal capable of fertilizing an egg of a female animal of the species of the paternal male animal and methods of producing and using the reduced dose inseminate for in vivo or in vitro fertilization for the production of embryos and offspring of the species of the paternal animal.

Specifically, a reduced dose inseminate produced by combining a plurality of paternal sperm cells obtained from a paternal mammal with a plurality of heterogeneous sperm cells obtained from a heterogeneous male animal and methods of producing and using the reduce dose inseminate for the in vivo and in vitro fertilization for the production of embryos and offspring of the species of the paternal animal.

Figure 1:
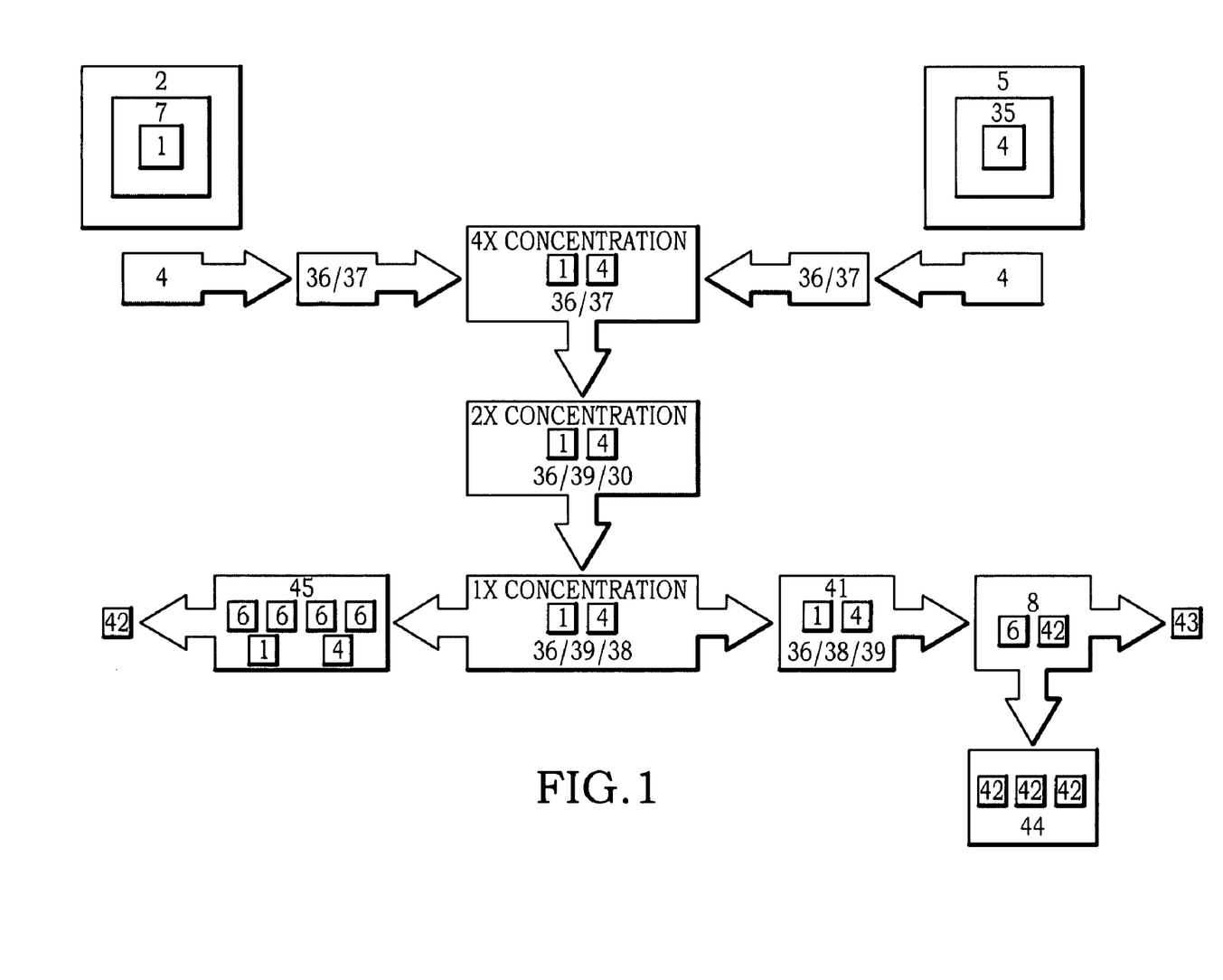
FIG. 1 is a block diagram which shows how to make and use an embodiment of the inventive reduced dose inseminate.

Now referring to primarily to FIG. 1, fertilization efficiency of a plurality of paternal sperm cells (1) obtained from a paternal animal (2) used in a reduced dose inseminate (3) can be increased when supplemented with a plurality of heterogeneous sperm cells (4) obtained from a heterogeneous animal (5). The reduced dose inseminate (3) supplemented with a plurality of heterogeneous sperm cells (4) can perform as well as a conventional dose inseminate which contains a substantially greater amount of paternal semen (7) or a greater number of the plurality of paternal sperm cells (1).

For the purposes of this invention, the term "paternal animal" means a male animal from which an amount of paternal semen (7) can be obtained. Without limitation to the forgoing, the male animal will typically be a male mammal being a species of: horse, cattle, camel, deer, pig, sheep, goat, dog, cat, lion, whale, dolphin, porpoise, seal, hare, rabbit, elephant, mouse, rat, or other male mammal from which the amount of paternal semen (7) can be obtained by collection. However, as to certain embodiments of the invention, the paternal animal (2) can also be a male fish and without limiting the forgoing can be a species: salmon, tuna, sturgeon, halibut, catfish, or other male fish from which an amount of paternal semen (7) can be obtained by collection. As to other certain embodiments of the invention the paternal animal (2) can be a male bird and without limiting the forgoing can be a species: chicken, turkey, eagle, falcon, ostrich, emu, duck, goose, or other male bird from which an amount of paternal semen (7) can be collected.

For the purposes of this invention, the term "paternal semen" refers to seminal fluid which contains a plurality of paternal sperm cells (1) (sperm cells are also commonly referred to as "spermatozoa") capable of fertilizing an egg (6)(an egg is also commonly referred to as an "ova") obtained from a female of the same species (8) as the paternal animal (1). The amount of paternal semen (7) can be obtained from the paternal animal (1) by any means which produces a sufficient plurality of paternal sperm cells (1) for use in a reduced dose inseminate (3). By way of example, and without limiting the forgoing, the amount of paternal semen (7) can be collected from a paternal animal (2) by a variety of methods such as use of an artificial vagina, manual manipulation of the penis, electrical manipulation of the anus, or the like.

For the purposes of this invention, the term "paternal sperm cells" refers to the sperm cells contained in the amount of paternal semen (7) obtained from the paternal animal (2).

For the purposes of this invention, the term "sex-selected paternal sperm cells" refers to a plurality of paternal sperm cells (1) of an amount of paternal semen (7) obtained from a paternal animal (2) which have been separated into an X-chromosome bearing population (9) and a Y-chromosome bearing population (10). Any manner or method by which the X-chromosome bearing sperm cells (11) can be separated or sorted from the Y-chromosome bearing sperm cells (12) of an amount of paternal semen (2) to provide viable sex-selected paternal sperm cells (13) for use in the reduced dose inseminate (3) can be suitable for use.

Figure 2:
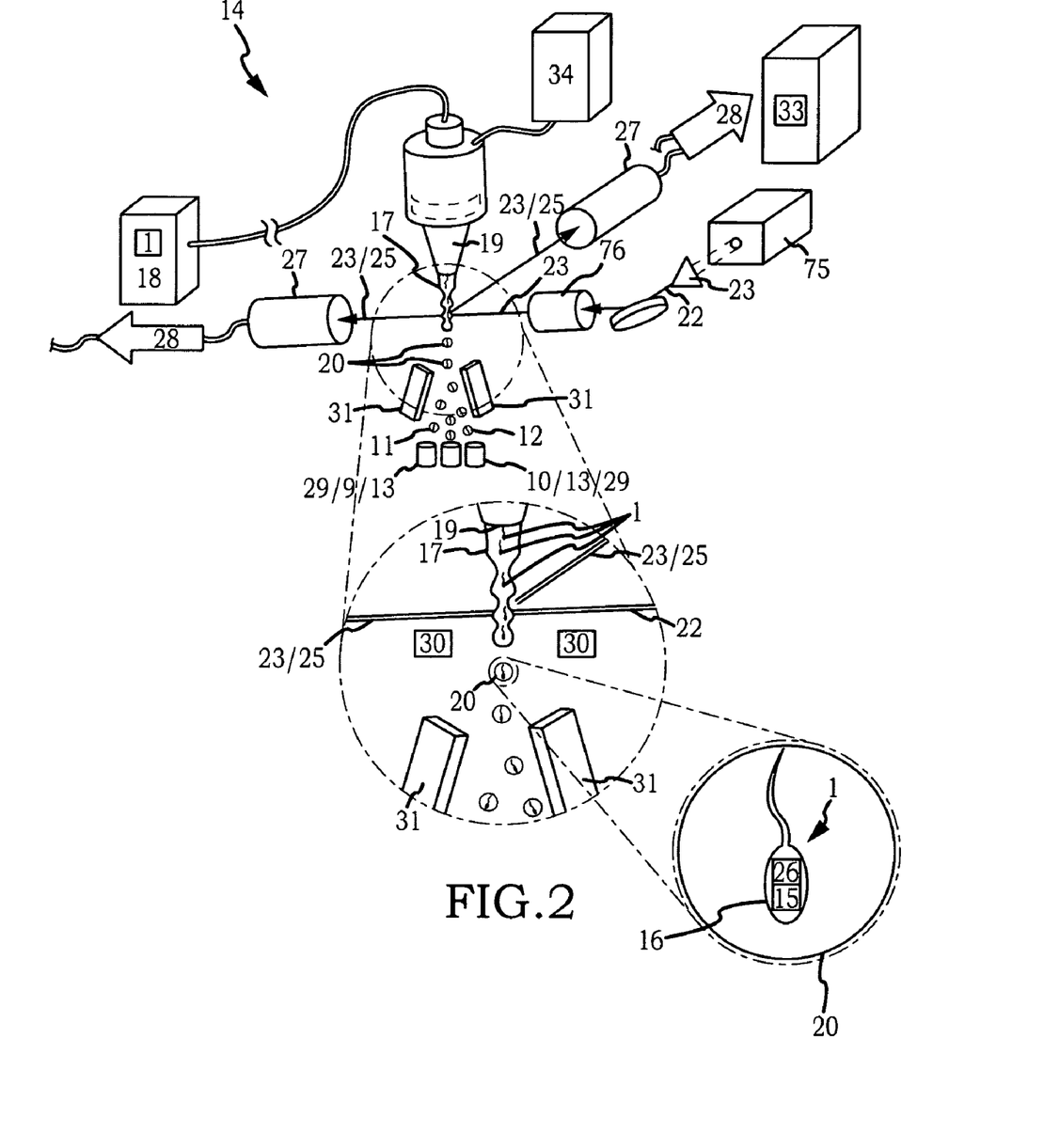
FIG. 2 is an illustration which shows a particular method of how to obtain sex-selected sperm cells of a paternal animal.

Now referring to FIG. 2, without limiting the forgoing, X-chromosome bearing sperm cells (11) can be separated or isolated from Y-chromosome bearing sperm cells (13) of the amount of paternal semen (7) using a flow cytometer (14). The flow cytometer (14) can be configured to differentiate and sort the plurality of paternal sperm cells (1) based on the amount of deoxyribonucleic acid ("DNA") (15) within the sperm head (16). Typically, a sheath fluid source (34) delivers a fluid stream (17) in which to entrain the plurality of paternal sperm cells (1) delivered from a sperm cell source (18). The fluid stream (17) having a plurality of paternal sperm cells (1) entrained can be oscillated by a nozzle (19) to generate a plurality of droplets (20) below the nozzle (19). Each of the plurality of droplets (20) can entrain one of the plurality of paternal sperm cells (1). An illumination source (21), such as a laser, can emit a beam of light (22), or a plurality of beams of light can be generated by utilizing a beam splitting element (23)(the beam splitting element shown but not the plurality of beams of light)(or by utilizing a plurality of illumination sources (21)), which can be focused incident upon the plurality of paternal sperm cells (1) entrained in the fluid stream (17) below the nozzle (19) through an optical element (24), either as a single beam of light (22) or a plurality of beams of light, whether at the same or different wave lengths. Characteristics of the beam of light (22) can be altered by incidence upon each one of the plurality of paternal sperm cells (1) within the fluid stream (17), or an emission (25) can be generated by incidence of the beam of light (22) upon ligands (26), fluorescent materials, or the like, bound to the DNA (15) of each one of the plurality of paternal sperm cells (1). The beam(s) of light (22) having altered characteristics or the emission (25) can be received by a single or a plurality of detectors (27) which can generate a signal (28) for analysis by a computer implemented program (33) to differentiate each one of the plurality of paternal sperm cells (1) correspondingly entrained in each one of the plurality of droplets (20) based upon one or a plurality of sperm cell characteristics. Each differentiated one of the plurality of paternal sperm cells (1) can be separated based upon the presence or absence of one or a plurality of the analyzed sperm cell characteristics collected in a corresponding one of a plurality of collection elements (29). The flow cytometer (14) can further include a droplet charge generator (30) which induces a positive or negative charge in each one of the plurality of droplets (20) and a droplet deflector (31) which acts upon each one of the charged plurality of droplets (20) to establish a trajectory to the proper one of the plurality of collection elements (29). Each of the plurality of collection elements (29) thereby contains a population of the plurality of paternal sperm cells (1) which can be predominantly X-chromosome bearing sperm cells (11) or Y-chromosome bearing sperm cells (12). The purity of the X-chromosome bearing population (9) or the Y-chromosome bearing population (10) can exceed 80% or 90% or can be of even greater purity depending upon the parameters of operating the flow cytometer (14); however, the purity level can be adjusted to be a greater or a lesser percent purity consistent with any particular application. Non-limiting examples of conventional methods of using a flow cytometer (14) to sort the plurality of paternal sperm cells (1) suitable for use in the production of a reduced dose inseminate (2) are described in U.S. Pat. Nos. 5,135,759; 6,372,422; 7,195,920 and 7,169,548, each hereby incorporated by reference in the entirety herein.

Figure 3:
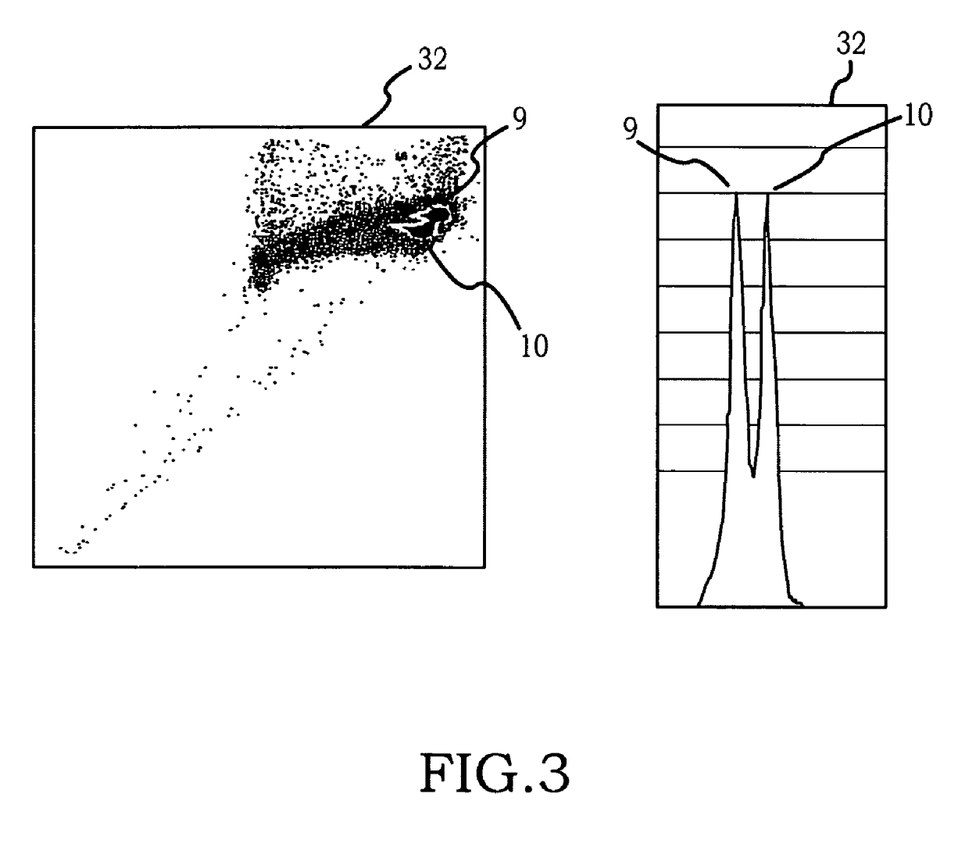
FIG. 3 is an illustration which shows a bivariate plot of paternal sperm cells separated into an X-chromosome bearing population and a Y-chromosome bearing population.

Now referring primarily to FIG. 3, a bivariate plot (32) can be generated during the use of a flow cytometer (14) to separate or sort a plurality of paternal sperm cells (1) into an X-chromosome bearing population (9) and Y-chromosome bearing population (10) as above-described is shown. The bivariate plot (32) shows that a mixture of X-chromosome bearing sperm cells (11) and Y-chromosome bearing sperm cells (12) in an amount of paternal semen (7) can be resolved into an X-chromosome bearing population (9) and a Y-chromosome bearing population (10) of paternal sperm cells (1).

For the purposes of this invention, the term "heterogeneous animal" refers to an animal which is not of the same species as the paternal animal (2). As one example, the paternal animal (2) can be a bovine animal then the heterogeneous animal (5) can be any other species of animal. In certain instances, the heterogeneous animal (5) could be an animal of the same species as the paternal animal (2) but whose sperm cells are incapable of fertilizing the egg (6) of a female animal the same species (8) as the paternal animal (2). For example, a bovine male animal (or individual of other species of animal) with a genetic deficiency in sperm production which produces sperm cells which are motile but incapable of fertilizing an egg (6) the non-fertile sperm cells can be combined with the fertile plurality of sperm cells (1) of the paternal animal (2) as the heterogeneous sperm cells (4).

For the purposes of this invention the term "heterogeneous semen" refers to seminal fluid which contains a plurality of heterogeneous sperm cells (4) which are not capable of fertilizing an egg (6) obtained from a female of the same species (8) as the paternal animal (2). An amount of heterogeneous semen (35) can be obtained from a heterogeneous animal (5) by any means which produces a sufficient plurality of heterogeneous sperm cells (4) for use in a reduced dose inseminate (3). By way of example, and without limiting the forgoing, an amount of heterogeneous semen (35) can be collected from a heterogeneous animal (5) by a variety of methods such use of an artificial vagina, manual manipulation of the penis, electrical manipulation of the anus, or the like.

For the purposes of this invention, the term "heterogeneous sperm cells" refers to sperm cells contained in an amount of heterogeneous semen (35). For clarity purposes, a plurality of heterogeneous sperm cells (4) are sufficiently different from the plurality of paternal sperm cells (1) such that an egg (6) obtained from a female animal of the same species (8) as the paternal animal (2) cannot be fertilized by the plurality of heterogeneous sperm cells (4); however, the term is not intended to infer or relate to differences between individual sperm cells in the heterogeneous semen (35).

For the purposes of this invention, the term "extender" refers to a solution that comes in contact with the plurality of paternal sperm cells (1) or the plurality of heterogeneous sperm cells (4), whether as isolated populations or combined in the reduced dose inseminate (3), typically for the purpose of dilution or as a cryoprotectant. Typical examples of an extender (36) can contain one or more of: sodium citrate, Tris[hydroxymethyl]aminomethane (also referred to as "TRIS"), TES (N-Tris [Hydroxymethyl]methyl-2-aminoethanesulfonic acid), monosodium glutamate, HEPES medium such as HEPES buffered-medium, HEPES buffered bovine gamete medium and particularly HBGM3 and can further contain cryoprotectants such as glycerol, dimethyl sulfoxide, ethylene glycol, propylene glycol; other organic substances such as egg yolk, an egg yolk extract, milk, a milk extract, casein, albumin, lecithin, bovine serum albumin, cholesterol; sugars such as the monosacharides, glucose, fructose, or mannose; detergents such as sodium dodecyl sulfate; antioxidants such butylated hydroxytoluene; capacitation facilitators such as alpha amylase, beta amylase, or beta glucuronidase; antibiotics such as tylosin, gentamicin, lincomycin, spectinomycin, linco-spectin (a combination of lincomycin and spectinomycin), penicillin, streptomycin, and ticarcillin; flow cytometer sheath fluids; and specifically without limiting the forgoing the particular extenders (36) referred to below as TRIS-A (37) and TRIS-B (38); although the inventive reduced dose inseminate (3) or methods of using a reduced dose inseminate (3) are not limited by the working examples which use TRIS-A as an extender (36) to dilute concentration of the plurality of paternal sperm cells (1) and the plurality of the homogeneous sperm cells (4) or which use TRIS-B (38) as a cryoprotectant (39).

For the purposes of this invention the term "TRIS-A" refers to an extender (36) having the formulation in Table 1.

TABLE 1

| TRIS-A Extender. | |
| --- | --- |
| TRIS | 200 mM |
| Citric Acid | 65 mM |
| Fructose | 56 mM |
| Egg Yolk* | 20% by volume |
| Hydrochloric Acid | addition to pH 6.8 |

*Egg Yolk can be clarified by winterization process to remove certain particulates and fats.

The formulation of TRIS-A set out in Table 1 can from application to application of the invention be modified to increase viability or reduce damage to the plurality of paternal sperm cells (1) or the plurality of the homogeneous sperm cells (4) and the above formulation is provided as a non-limiting example of a numerous and wide variety of similar extenders which are suitable for use in making or using the reduced dose inseminate (3). See also, Yassen, A. M. and Foote, R. H., *Freezability of Bovine Spermatozoa in Tris-Buffered Yolk Extenders Containing Different Levels of Tris, Sodium, Potassium and Calcium Ions*, J. Dairy Science, Vol. 50, No. 6, 887-892 (1966), hereby incorporated by reference in the entirety herein. Extenders (36) in general and specifically the particular extender TRIS-A (37) can further include one or more antibiotics (40) as above described or consistent with animal health regulations of any particular jurisdiction. Also, the description of TRIS-A is not intended to limiting with respect to the wide variety of extenders (36) which can be utilized in making and using certain embodiments of the reduce dose inseminate (3) as described above.

For the purposes of this invention the term "TRIS-B" refers to an extender having the formulation in Table 2.

TABLE 2

| TRIS | 200 mM |
| --- | --- |
| Citric Acid | 65 mM |
| Fructose | 56 mM |
| Egg Yolk* | 20% by volume |
| Glycerol | 12% by volume |
| Hydrochloric Acid | addition to pH 6.8 |

*Egg Yolk can be clarified by winterization process to remove certain particulates and fats.

The formulation of TRIS-B set out in Table 2 can from application to application of the invention be modified to increase viability or reduce damage to the plurality of paternal sperm cells (1) or the plurality of the homogeneous sperm cells (4) and the above formulation is provided as a non-limiting example of a numerous and wide variety of similar extenders which are suitable for use in making or using the reduced dose inseminate (3). Again see for example, Yassen, A. M. and Foote, R. H., *Freezability of Bovine Spermatozoa in Tris-Buffered Yolk Extenders Containing Different Levels of Tris, Sodium, Potassium and Calcium Ions*, J. Dairy Science, Vol. 50, No. 6, 887-892 (1966). Extenders (36) in general and specifically the particular extender TRIS-B (38) can further include one or more antibiotics (40) as above described or consistent with animal health regulations of any particular jurisdiction. Additionally, while TRIS-B (38) of the particular formulation set out in Table 2 uses glycerol as a cryoprotectant (39) the invention is not so limited. Also, the description of TRIS-B is not intended to limiting with respect to the wide variety of extenders (36) which can be utilized in making and using certain embodiments of the reduce dose inseminate (3) as described above.

Again referring primarily to FIG. 1, for the purpose of this invention the term "reduced dose inseminate" refers to a plurality of paternal sperm cells (1) combined with a plurality of heterogeneous sperm cells (4) without limitation to any particular dosage form (41). As to particular embodiments, the plurality of paternal sperm cells (1) and the plurality of heterogeneous sperm cells (4) can be contained in a corresponding amount of paternal semen (7) and heterogeneous semen (35) which may be diluted with an extender (36) prior to or after combination. As to other particular embodiments, the plurality of paternal sperm cells (1) can be sex-selected paternal sperm cells (13) to provide an X-chromosome bearing population (9) or a Y-chromosome bearing population (10) which can be combined with the plurality of heterogeneous sperm cells (4). As to yet other particular embodiments, the reduced dose inseminate (3) may be an amount by volume of the combination of the plurality of paternal cells (1) (whether or not sex-selected paternal sperm cells (13)) and the heterogeneous sperm cells (4) along with an amount of an extender (36). The volume of the combination of paternal sperm cells (1) and heterogeneous sperm cells (4) and the concentration or the ratio of the paternal sperm cells (1) and heterogeneous sperm cells (4) within a volume can vary depending on the application. Other particular embodiments of the reduced dose inseminate (3) can further include a particular dosage form (41). As one non-limiting example, the dosage form (41) for artificial insemination of cattle can be a one-quarter cubic centimeter (0.25 cc) artificial insemination straw which contains the reduced dose inseminate (3). When a reduced dose inseminate (3), the combination of paternal sperm cells (1) and heterogeneous sperm cells (4), is otherwise produced by the same steps or procedures as any particular conventional insemination dose, the resulting reduced dose inseminate (3) can by comparison contain fewer paternal sperm cells (1)(hence a reduced dose or low dose of paternal sperm cells (1)) capable of fertilizing an egg (6) of a female of the same species as the paternal animal (2).

As a general non-limiting example, a reduced dose inseminate (3) which contains a reduced dose (or low dose) of paternal sperm cells (1) can be made by obtaining an amount of paternal semen (7) or an amount of sex-selected paternal sperm cells (1 3)(as to each fresh or cryopreserved) of a paternal animal (2) such as a bull, stallion, ram, bill goat, boar, or otherwise. The amount of paternal semen (7) or sex-selected paternal sperm cells (13) can be extended with TRIS-A (38) extender (or other extender (36)) to achieve a concentration of the extended plurality of paternal sperm cells (1) of about four times greater than the concentration of the plurality of paternal sperm cells (1) in the particular embodiment of the reduced dose inseminate (3) to be produced. Embodiments of the reduced dose inseminate (3) will typically have a concentration of the plurality of paternal sperm cells (1) in a range of about 200,000 paternal sperm cells (1) per milliliter and about 40 million paternal sperm cells (1) per milliliter depending upon various factors such as the species of the paternal animal (2), the scarcity of the paternal semen (7), the fertility of the paternal semen (7), the dosage form (41), the method of insemination (whether artificial insemination or in vitro fertilization), whether for multiple ovulation embryo transfer or single ovulation single embryo production, the female animal of the same species as the paternal animal (2) being inseminated, or the like. Accordingly, the four times concentration of the paternal sperm cells (1) in TRIS-A (37) (or other extender) can be in a range of about 800,000 paternal sperm cells (1) per milliliter and about 160 million paternal sperm cells (1) per milliliter of TRIS-A (37).

The extended paternal semen (7) or sex-selected paternal sperm cells (13) can be cooled to a temperature in a range of about 4 degrees Celsius ("° C.") and about 5° C. The cooled extended paternal semen (7) or sex-selected paternal sperm cells (13) can be held at this temperature to allow the membranes of the paternal sperm cells (1) to move toward equilibrium or equilibrate with the TRIS-A (typically a period of about 90 minutes or as to certain embodiments not less than 90 minutes). The cooled extended paternal sperm cells (7) can be held in this condition not to exceed a length of time in which the paternal sperm cells (7) remain viable or capable fertilizing an egg (6) of a female of the same species (8) as the paternal animal (2). Typically, the period of time held will not exceed 12 hours.

An amount of heterogeneous semen (35) can be obtained from a heterogeneous animal (5) (or as cryopreserved heterogeneous semen (35) of the heterogeneous animal (5). The heterogeneous semen (35) can be suspended in an amount of TRIS-A (37) (or other extender (36)) and then centrifuged in range of about 500 rounds per minute ("rpm") and about 5,000 rpm for a period in a range of between about one minute and about ten minutes. The supernatant can be decanted and the pellet containing the plurality of heterogeneous sperm cells (4) can be suspended in an amount of TRIS-A (37) to achieve a concentration of the plurality of heterogeneous sperm cells (4) of about four times greater than the concentration of the plurality of heterogeneous sperm cells (4) in the particular embodiment of the reduced dose inseminate (3) to be produced. Embodiments of the reduced dose inseminate (3) will typically have a concentration of the plurality of heterogeneous sperm cells (4) in a range of about 4 million heterogeneous sperm cells (4) per milliliter and about 80 million heterogeneous sperm cells (4) per milliliter depending upon various factors above described with regard to the paternal sperm cells (1) and the efficiency of the particular heterogeneous sperm cells (4) to enhance characteristics of the paternal sperm cells (1) such as viability, motility, fertility, or the like. Accordingly, four times concentration of the plurality of heterogeneous sperm cells (1) in TRIS-A (37)(or other extender (36)) can be in a range of about 16 million heterogeneous sperm cells (4) per milliliter and about 320 million heterogeneous sperm cells (1) per milliliter of TRIS-A (37).

The extended heterogeneous sperm cells (4) can be cooled to a temperature in a range of about 4° C. and about 5° C. The cooled extended heterogeneous sperm cells (4) can be held at this temperature to allow the membranes of the heterogeneous sperm cells (4) to move toward equilibrium or equilibrate with the TRIS-A (typically a period of about 90 minutes or as to certain embodiments not less than 90 minutes). The cooled extended heterogeneous sperm cells (4) can be held in this condition until combined with the paternal sperm cells (4).

About equal volumes of the cooled extended paternal sperm cells (1) or sex-selected paternal sperm cells (13) and the cooled extended heterogeneous sperm cells (4) can be combined to achieve two times greater concentration of each of the paternal sperm cells (1) or the heterogeneous sperm cells (4) with respect to the final concentration of each in the reduced dose inseminate (3) to be produced.

To the two fold concentrated combination of the plurality of paternal sperm cells (1) and heterogeneous sperm cells (4), about an equal volume of TRIS-B (38)(containing between about 12% and 20% glycerol) can be added and the mixture can be cooled to temperature in a range of about 4° C. and about 5° C. The cooled extended combination of paternal sperm cells (1) and heterogeneous sperm cells (4) can be held at this temperature to allow the membranes of the paternal sperm cells (1) and the heterogeneous sperm cells (4) to move toward equilibrium or equilibrate with the TRIS-B (typically a period in the range of about 30 minutes and about 90 minutes or as to certain embodiments not less than 90 minutes). The cooled extended combination of paternal sperm cells (7) and heterogeneous sperm cells (4) can be held in this condition not to exceed a length of time in which the paternal sperm cells (1) remain viable or capable fertilizing an egg (6) of a female of the same species as the paternal animal (2).

The cooled extended combination of paternal sperm cells (1) and heterogeneous sperm cells (4) can be handled by normal procedures utilized for producing doses of the paternal semen (7). Accordingly, as to certain embodiments, the cooled extended combination of paternal sperm cells (1) and heterogeneous sperm cells (4) can be aliquoted into 0.25 cc artificial insemination straws. The reduced dose inseminate (3) of this dosage form (41)(0.25 cc artificial insemination straw) provides a plurality of paternal sperm cells (1) typically in the range of about 50,000 and about 10 million and a plurality of heterogeneous sperm cells (4) in the range of about 1 million and about 20 million. However, a greater or lesser number of paternal sperm cells (1) can be included in the reduced dose inseminate (3) depending on the scarcity of the paternal semen (7) or sex-selected paternal sperm cells (13).

The reduced dose inseminate (3) can used for artificial insemination to fertilize the egg(s) (6) of a female of the same species (8) as the paternal animal (2) to for the production of embryos (42) whether as single embryo pregnancies to generate offspring (43) for meat or animal replacement or multiple embryo pregnancies for multiple ovulation embryo production and subsequent flushing of multiple embryos (44). Pregnancy rates resulting from the use of the inventive reduced dose inseminate (3) can be at the same level as when conventional dose inseminates are utilized in artificial insemination procedures.

Alternately, the reduced dose inseminate (3) can be used in vitro fertilization (45) procedures to fertilize eggs (6) of obtained from a female animal of the same species (8) to produce in vitro fertilized embryos (42).

A particular non-limiting example of a reduced dose inseminate (3) can be prepared by obtaining one milliliter of fresh paternal semen (7) from a bull of a bovine species of a dairy or beef breed (the paternal animal (2)). The one milliliter of fresh paternal semen (7) of a bull of a bovine species will typically contain about one billion paternal sperm cells (1) which can be extended with TRIS-A (37) to achieve a concentration of paternal sperm cells (1) of about 16 million per milliliter ("mL") in final volume of about 62.6 mL. The extended paternal semen (7) can be cooled to temperature in a range of about 4° C. and about 5° C. and held for period of about 90 minutes.

Twenty-five milliliters of fresh heterogeneous semen (35) can be obtained from a bill goat(s), each milliliter containing about one billion heterogeneous sperm cells (4), can be centrifuged at about 2000 rpm for about 5 minutes. The supernatant can be discarded and the heterogeneous sperm cells (4) extended with TRIS-A (37) to a concentration of heterogeneous sperm cells (4) of about 320 million per milliliter with a final volume of about 69.4 mL. The extended heterogeneous sperm cells (4) can be cooled to a temperature in a range of about 4° C. and about 5° C. and held for period of about 90 minutes.

About equal volumes of the cooled extended paternal sperm cells (1) and cooled extended heterogeneous sperm cells (4) (about 60 mL cooled extended bull semen about 16 million sperm cells per mL and about 60 mL cooled extended bill goat semen about 320 million sperm cells per mL) can be combined and extended to a total volume of about 240 mL with TRIS-B (38). The extended combination of paternal sperm cells (1) and heterogeneous sperm cells (4) can be cooled to a temperature in a range of about 4° C. and about 5° C. and held for period of about 30 minutes.

The cooled extended combination of paternal sperm cells (1) of a bovine bull and heterogeneous sperm cells (4) of a bill goat(s) at 4° C. can be aliquoted into a plurality of 0.25 mL artificial insemination straws (about 960 0.25 mL artificial insemination straws can be produced from the total volume of 240 mL) to produce a corresponding plurality of reduced dose inseminate (3) in the dosage form of a 0.25 mL artificial insemination straws. Each of the plurality of reduced dose inseminate (3) contain about one million paternal sperm cells (1) of a bovine bull and about 20 million heterogeneous sperm cells (4) of the bill goat(s). The plurality of reduced dose inseminate (3) were frozen by conventional cryopreservation procedures.

Artificial insemination using a single frozen-thawed reduced dose inseminate (3) in a single estrus cycle in the dosage form of a 0.26 mL artificial insemination straw produced as above described were used to artificially inseminate 118 female bovine animals of the species (8) of the paternal animal (2) (118 cows) by otherwise conventional artificial insemination procedures resulting in 66 pregnancies (56% pregnancy rate). These results show that use of the inventive reduced dose inseminate (3) in conventional artificial insemination procedures can achieve pregnancy rates comparable to the use of a normal dose inseminate (a normal dose inseminate can contain about 20 million paternal sperm cells of a bull of a bovine species) in control groups in which a pregnancy rate of between about 50% and about 65% can be achieved.

A second particular non-limiting example of a reduced dose inseminate (3) can be prepared by obtaining one milliliter of fresh paternal semen (7) from a bill goat (the paternal animal (2)). The one milliliter of fresh paternal semen (7) of the bill goat will typically contain about one billion paternal sperm cells (1) which can be extended with TRIS-A (37) to achieve a concentration of paternal sperm cells (1) of about 32 million per milliliter ("mL") in final volume of about 31.3 mL. The extended paternal semen (7) can be cooled to temperature in a range of about 4° C. and about 5° C. and held for period of about 90 minutes.

Fifteen milliliters of fresh heterogeneous semen (35) can be obtained from a ram(s), each milliliter containing about one billion heterogeneous sperm cells (4), can be centrifuged at about 2000 rpm for about 5 minutes. The supernatant can be discarded and the heterogeneous sperm cells (4) extended with TRIS-A (37) to a concentration of heterogeneous sperm cells (4) of about 320 million per milliliter with a final volume of about 46.9 mL. The extended heterogeneous sperm cells (4) can be cooled to a temperature in a range of about 4° C. and about 5° C. and held for period of about 90 minutes.

About equal volumes of the cooled extended paternal sperm cells (1) and cooled extended heterogeneous sperm cells (4) (about 30 mL cooled extended bill goat semen about 32 million sperm cells per mL and about 30 mL cooled extended ram semen about 320 million sperm cells per mL) can be combined and extended to a total volume of about 120 mL with TRIS-B (38). The extended combination of paternal sperm cells (1) and heterogeneous sperm cells (4) can be cooled to a temperature in a range of about 4° C. and about 5° C. and held for period of about 30 minutes.

The cooled extended combination of paternal sperm cells (1) of a bill goat and heterogeneous sperm cells (4) of a ram(s) at 4° C. can be aliquoted into a plurality of 0.25 mL artificial insemination straws (about 480 0.25 mL artificial insemination straws can be produced from the total volume of 120 mL) to produce a corresponding plurality of reduced dose inseminate (3) in the dosage form of a 0.25 mL artificial insemination straws. Each of the plurality of reduced dose inseminate (3) contain about two million paternal sperm cells (1) of a bill goat and about 20 million heterogeneous sperm cells (4) of the ram. The plurality of reduced dose inseminate (3) were frozen by conventional cryopreservation procedures.

Artificial insemination by laproscopic uterus insemination using a single frozen-thawed reduced dose inseminate (3) in a single estrus cycle in the dosage form of a 0.25 mL artificial insemination straw produced as above described for 125 female goat cows by otherwise conventional artificial insemination by laproscopic uterus insemination procedures resulting in 64 pregnancies (51% pregnancy rate). These results show that use of the inventive reduced dose inseminate (3) can achieve pregnancy rates comparable to the use of a normal dose inseminate (a normal dose inseminate can contain about 20 million paternal sperm cells of a bill goat).

For the purposes of this invention the term "artificial insemination" refers to the process by which the "reduced dose inseminate" is placed into the reproductive tract of a female animal of the same species (8) as the paternal animal (2) for the purpose of impregnating the female animal (8). Without limitation to the forgoing, certain embodiments of the invention can utilize intracervical insemination where the "reduced dose inseminate" can be injected high into the cervix. Other embodiments of the invention, can utilize intrauterine insemination of the "reduced dose inseminate" from which the sperm cells have been removed from most other components of the seminal fluids and can be injected directly into the uterus of the female animal. Yet other embodiments of the invention can include laproscopic artificial insemination of the female animal of the same species (8) as the paternal animal (2).

For the purposes of this invention the term "in vitro fertilization" refers to the process by which an egg (6) of a female animal of the same species (8) as the paternal animal (2) can be fertilized using a reduced dose inseminate (3) which includes paternal sperm cells (1) outside of the womb, in vitro. The process can involve hormonally controlling the ovulatory process, removing ova ("eggs")(6) from the female animal's (8) ovaries and allowing paternal sperm cells (1) of the reduced dose inseminate (3) fertilize them in a fluid medium. The egg(s)(6) removed from female animal's (8) ovaries can be cryopreserved and later fertilized in vitro. The resulting embryos (42) can then be transferred to the uterus of recipient female animal(s) with the intent to establish a successful pregnancy or cryopreserved for later implantation.

For purposes of the present invention, "embryo" refers to the stages of development whereby a fertilized egg (6) obtained from a female animal of the same species (8) as the paternal animal (2) develops toward a fetus (42), in vitro or in vivo.

In particular embodiments of the invention, the heterogeneous sperm cells (4) may be provided to an end user in the form of a kit designed to allow the end user to combine a sample of paternal semen (1) of known or unknown concentration with said heterogeneous sperm cells supplied in the kit to create a plurality of reduced dose inseminates (3).

A particular non-limiting example of a kit to a create reduced dose inseminate (3) can be prepared by providing a 0.50 cc straw of cryopreserved bull (bovine) semen containing 200 million sperm cells from a bull that produces sperm which is unable to fertilize (infertile bull is heterogeneous sperm cells (4) source) and a vial containing 4.0 ml of sterile liquid dilution extender such as TALP, TRIS A, Androhep, Triladyl, or the like. The contents of said 0.50 cc straw of heterogeneous sperm (4) is placed in said vial containing 4.5 ml of sterile liquid dilution extender to create a diluted portion of heterogeneous sperm at concentration of about 20 million sperm per ml.

The end user of the kit provides a frozen straw of commercially available bovine semen (bull is paternal sperm (1) source) which is thawed to provide about 10 million paternal sperm (1) in a volume of about 0.50 ml.

The said thawed about 10 million paternal sperm (1) is placed into said vial containing about 5 ml of heterogeneous sperm (4) at about 20 million sperm per ml to generate a mixture containing about 2 million paternal sperm (1) and 20 million heterogeneous sperm (4) per ml.

The end user uses empty 0.5 cc cryopreservation straws to draw up about 0.5 cc of said mixture of paternal and heterogeneous sperm to provide a reduced dose inseminate (3) of a volume of about 0.5 ml containing about 1 million paternal sperm (1) and about 10 million heterogeneous sperm (4). Since the end user is able to fill about 10 of said empty 0.5 cc cryopreservation straws, the number of usable reduced dose inseminates (3) provided by the kit is about 10 times greater than the number of paternal sperm (1) straws originally thawed. In this way, the number of breedings from a genetically valuable bull can be increased by a multiple.

For the purpose of the present invention, the term "combination or combining or combined" refers to any method of putting two or more materials together. Such methods include, but are not limited to, mixing, commingling, incorporating, intermingling, stirring, integrating, or the like.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a sperm cell" refers to one or more of sperm cells. As such, the terms "a" or "an", "one or more" and "at least one" can be used interchangeably herein unless otherwise indicated. According to the present invention, an isolated material or particle is removed from its natural milieu; however, an isolated material does not necessarily reflect the extent to which the material or particle has been purified.

As can be easily understood from the foregoing, the basic concepts of the present invention may be embodied in a variety of ways. The invention involves numerous and varied embodiments of a reduced dose inseminate (3) and methods of making and using such a reduced dose inseminate (3). As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "flow sorter" should be understood to encompass disclosure of the act of "flow sorting"—whether explicitly discussed or not—and, conversely, were there effectively disclosure of the act of "flow sorting", such a disclosure should be understood to encompass disclosure of a "flow sorter" and even a "a means for flow sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the reduced dose inseminates herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

In addition, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A dosage of inseminate, comprising:
   a) a plurality of sex-selected paternal sperm cells obtained from a paternal male bovine;
   b) a plurality of heterogeneous sperm cells comprising a plurality of infertile bovine sperm cells or a plurality of sperm cells obtained from an animal other than a bovine, wherein said plurality of sex-selected paternal sperm cells contained in said dosage of inseminate is capable of achieving fertilization of an egg of a female bovine; and
   c) an extender.

2. The dosage of inseminate as described in claim 1, wherein said plurality of sex-selected paternal sperm cells comprises a number fewer than the number of said plurality of heterogeneous sperm cells.

3. The dosage of inseminate as described in claim 2, wherein said plurality of sex-selected paternal sperm cells comprises between about 5 percent and about 50 percent the number of heterogeneous sperm cells.

4. The dosage of inseminate as described in claim 3, wherein said plurality of sex-selected paternal sperm cells comprises a range of about one hundred thousand to about ten million sperm cells and wherein said plurality of heterogeneous sperm cells comprises a range of about two million to about twenty million sperm cells.

5. The dosage of inseminate as described in claim 4, further comprising a dosage form comprising a 0.25 cc artificial insemination straw in which contains said dosage of inseminate.

6. The dosage of inseminate as described in claim 1, wherein said plurality of heterogeneous sperm cells comprises a plurality of sperm cells obtained from an animal other than a bovine.

7. The dosage of inseminate as described in claim 1, wherein said plurality of heterogeneous sperm cells comprises a plurality infertile sperm cells incapable of fertilization of said egg of said female bovine.

8. The dosage of inseminate as described in claim 1, wherein the extender comprises one or more selected from the group consisting of: sodium citrate, Tris[hydroxymethyl]aminomethane, TES (N-Tris[Hydroxymethyl]methyl-2-aminoethanesulfonic acid), monosodium glutamate, HEPES buffered medium, HEPES buffered bovine gamete medium, HBGM3, and combinations thereof.

9. The dosage of inseminate as described in claim 8, wherein the extender further comprises a cryoprotectant selected from the group consisting of: glycerol, dimethyl sulfoxide, ethylene glycol, propylene glycol, and combinations thereof.

10. The dosage of inseminate as described in claim 8, wherein the extender further comprises an organic substances selected from the group consisting of: egg yolk, egg yolk extract, milk, milk extract, casein, albumin, lecithin, bovine serum albumin, cholesterol, and combinations thereof.

11. The dosage of inseminate as described in claim 8, wherein the extender further comprises a sugar selected from the group consisting of: monosacharides, glucose, fructose, mannose, and combinations thereof.

12. The dosage of inseminate as described in claim 8, wherein the extender further comprises a detergent.

13. The dosage of inseminate as described in claim 8 further comprising an antioxidant.

14. The dosage of inseminate as described in claim 8, wherein the extender further comprises a capacitation facilitator selected from the group consisting of: alpha amylase, beta amylase beta glucuronidase, and combinations thereof.

15. The dosage of inseminate as described in claim 8, wherein the extender further comprises an antibiotic selected from the group consisting of: tylosin, gentamicin, lincomycin, spectinomycin, linco-spectin, penicillin, streptomycin, and ticarcillin, and combinations thereof.

* * * * *